(12) United States Patent
Sanderson et al.

(10) Patent No.: US 6,376,499 B1
(45) Date of Patent: *Apr. 23, 2002

(54) THROMBIN INHIBITORS

(75) Inventors: Philip E. Sanderson, Philadelphia; Terry Lyle, Lederach; Bruce Dorsey, Maple Glen; Matthew G. Stanton; Adel M. Naylor-Olsen, both of Lansdale, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/428,314

(22) Filed: Oct. 28, 1999

Related U.S. Application Data

(60) Provisional application No. 60/106,294, filed on Oct. 30, 1998.

(51) Int. Cl.[7] ............... A61K 31/497; C07D 403/12; C07D 405/14; C07D 413/12; C07D 487/04
(52) U.S. Cl. .................. 514/255.05; 544/405
(58) Field of Search ............... 544/405; 514/255.05

(56) References Cited

U.S. PATENT DOCUMENTS

| | | |
|---|---|---|
| 5,260,307 A | 11/1993 | Ackermann et al. |
| 5,405,854 A | 4/1995 | Ackermann et al. |
| 5,455,348 A | 10/1995 | Austel et al. |
| 5,459,142 A | 10/1995 | Tone et al. |
| 5,510,369 A | 4/1996 | Lumma et al. |
| 5,744,486 A | 4/1998 | Sanderson et al. |
| 5,866,573 A | 2/1999 | Sanderson et al. |
| 5,981,546 A | 11/1999 | Duggan et al. |
| 6,180,627 B1 * | 1/2001 | Blagg et al. ............ 514/235.8 |

FOREIGN PATENT DOCUMENTS

| | | |
|---|---|---|
| EP | 0 262096 A1 | 9/1987 |
| EP | 0509769 A2 | 4/1992 |
| WO | WO 94/25051 | 11/1994 |
| WO | WO 96/11697 | 4/1996 |
| WO | WO 96/31504 | 10/1996 |
| WO | WO 96/32110 | 10/1996 |
| WO | WO 97/01338 | 1/1997 |
| WO | WO 97/40024 | 10/1997 |
| WO | WO 99/11267 | 3/1999 |

OTHER PUBLICATIONS

Kitazawa, et al.., "Preparation of 1,4-disubstituted cyclic amino derivatives as serotonin antagonists," Database CA on Stn., Chem. Abs., vol. 129: 302552 (1998).

Peter R. Berstein, et al., "Nonpeptidic Inhibitors of Human Leukocyte Elastase . . . " J. Med. Chem., vol. 37, 1994, pp. 3313–3326.

Sanderson, et al., "Preparation of 3–amino–2–pyrazinone–1–acetamide derivatives as thrombin inhibitors," Chem. Abstracts (The Amer. Chem. Soc.), vol. 128, No. 3, pp. 532–533, 22922r, Jan. 19, 1998.

* cited by examiner

Primary Examiner—Emily Bernhardt
(74) Attorney, Agent, or Firm—Richard S. Parr; Valerie J. Camara

(57) ABSTRACT

Compounds of the invention are useful in inhibiting thrombin and associated thrombotic occlusions having the following structure:

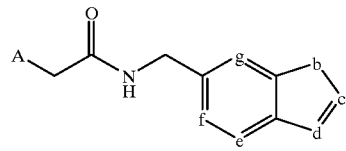

or a pharmaceutically acceptable salt thereof, wherein b is N $Y^1$ or O; c is $CY^2$ or N; d is $CY^2$; e is $CY^1$ or N; f is $CY^1$ or N; g is $CY^1$ or N; $Y^1$ is hydrogen, $C_{1-4}$ alkyl, or halogen; $Y^2$ is hydrogen, $C_{1-4}$ alkyl, $C_{3-7}$ cycloalkyl, halogen, $NH_2$, OH or $C_{1-4}$ alkoxy;

A is

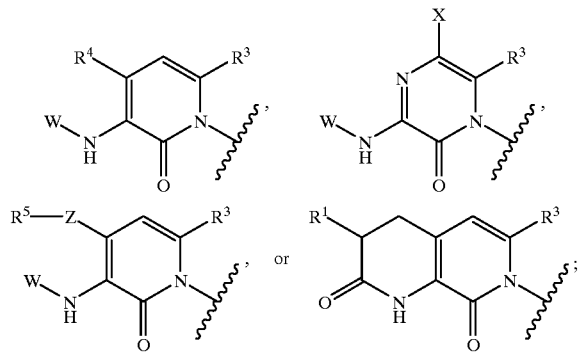

and W, X, Z, $R^3$, $R^4$ and $R^5$ are defined in the specification.

5 Claims, No Drawings

THROMBIN INHIBITORS

CROSS-REFERENCE TO RELATED APPLICATION

This application claims priority to provisional application No. 60/106,294, filed Oct. 30, 1998.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.*, (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or aketo carboxyl derivatives.

R. J. Brown et al., *J. Med. Chem.*, Vol. 37, pages 1259–1261 (1994) describes orally active, non-peptidic inhibitors of human leukocyte elastase which contain trifluoromethylketone and pyridinone moieties.

H. Mack et al., *J. Enzyme Inhibition*, Vol. 9, pages 73–86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention, useful as thrombin inhibitors and having therapeutic value in for example, preventing coronary artery disease, have the following structure:

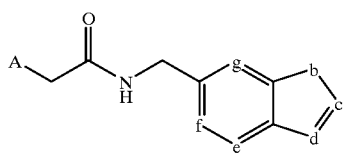

or a pharmaceutically acceptable salt thereof, wherein b is $NY^1$ or O; c is $CY_2$ or N; d is $CY^3$; e is $CY^4$ or N; f is $CY^5$ or N; g is $CY^6$ or N; $Y^4$, $Y^5$, and $Y^6$ are independently hydrogen, $C_{1-4}$ alkyl, or halogen; $Y^1$, and $Y^2$ are independently hydrogen, $C_{1-4}$ alkyl, $C_{3-7}$ cycloalkyl, halogen, $NH_2$, OH or $C_{1-4}$ alkoxy, and $Y_3$ is hydrogen, $C_{1-4}$ alky, $C_{3-7}$ cycloalkyl, halogen, $NH_2$, OH, CN or $C_{1-4}$ alkoxy;

A is

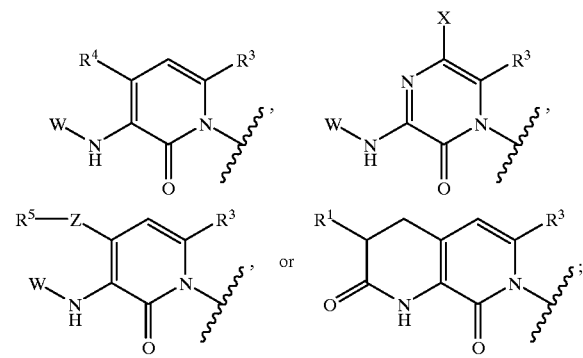

W is
  hydrogen,
  $R^1$,
  $R^1OCO$,
  $R^1CO$,
  $R^1SO_2$,
  $R^1(CH_2)_nNHCO$, or
  $(R^1)_2CH(CH_2)_nNHCO$,
    wherein n is 0–4;

$R^1$ is
  $R^2$,
  $R^2(CH_2)_mC(R^8)_2$, where m is 0–3, and each $R^8$ can be the same or different,
  $(R^2)(OR^2)CH(CH_2)_p$, where p is 1–4,

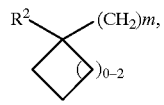

where m is 0–3,
  $R^2C(R^8)_2(CH_2)_m$, wherein m is 0–3, and each $R^8$ can be the same or different, wherein $(R^8)_2$ can also form a ring with C represented by $C_{3-7}$ cycloalkyl,
  $R^2CH_2C(R^8)_2(CH_2)_q$, wherein q is 0–2, and each $R^8$ can be the same or different, wherein $(R^8)_2$ can also form a ring with C represented by $C_{3-7}$ cycloalkyl,
  $(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicyclic alkyl, $C_{10-16}$ tricylic alkyl, or a 5- to 7-membered mono- or bicyclic heterocyclic ring which can be saturated or unsaturated, and which contains from one to three heteroatoms selected from the group consisting of N, O and S, $R^2O(CH_2)_p$, wherein p is 1–4,
$R^2CF_2C(R^8)_2$,
$(R^2CH_2)(R^2CH_2)CH$, or
$R^2SO_2$,
$R^2CH_2SO_2$,
$R^2(COOR^6)(CH_2)_r$, where r is 1–4;

$R^2$ and $R^5$ are independently
hydrogen,
phenyl, unsubstituted or substituted with one or more of $C_{1-4}$ alkyl, $C_{1-4}$ alkoxy, halogen, hydroxy, COOH, $CONH_2$, $CH_2OH$, $CO_2R^7$, where $R^7$ is $C_{1-4}$ alkyl, or $SO_2NH_2$,
naphthyl,
biphenyl,
5- to 7-membered mono- or a 9- to 10-membered bicyclic heterocyclic ring or non-heterocyclic ring which can be saturated or unsaturated, wherein the heterocyclic ring contains from one to four heteroatoms selected from the group consisting of N, O and S, and wherein the heterocyclic or non-heterocyclic ring is unsubstituted or substituted with halogen or hydroxy,
$C_{1-7}$ alkyl, unsubstituted or substituted with one or more of hydroxy,
  COOH,
  amino,
  aryl,
  $C_{3-7}$ cycloalkyl,
  $CF_3$,
  $N(CH_3)_2$,
  —$C_{1-3}$alkylaryl, heteroaryl, or heterocycloalkyl,
  $CF_3$
$C_{3-7}$ cycloalkyl, unsubstituted or substituted with aryl,
$C_{7-12}$ bicyclic alkyl, or
$C_{10-16}$ tricyclic alkyl;

$R^3$, $R^4$ and $R^6$ are independently selected from the group consisting of
hydrogen,
halogen,
$C_{1-4}$ alkyl,
$C_{3-7}$ cycloalkyl,
trifluoromethyl,
CN,
$SCH_3$,
$SOCH_3$, or
$SO_2CH_3$;

X is
hydrogen, or
halogen;

Z is $CH_2$, S, or $SO_2$;

$R^8$ is
hydrogen,
phenyl, unsubstituted or substituted with one or more of $C_{1-4}$ alkyl, $C_{1-4}$ alkoxy, halogen, hydroxy, COOH, $CONH_2$,
halogen,
naphthyl,
biphenyl,
a 5- to 7-membered mono- or a 9- to 10-membered bicyclic heterocyclic ring which can be saturated or unsaturated, and which contains from one to four heteroatoms selected from the group consisting of N, O and S, $C_{1-4}$ alkyl, unsubstituted or substituted with one or more of hydroxy,
  COOH,
  amino,
  aryl,
  heteroaryl, or
  heterocycloalkyl,
  $CF_3$
$C_{3-7}$ cycloalkyl,
$C_{7-12}$ bicyclic alkyl, or
$C_{10-16}$ tricyclic alkyl A class of compounds of the invention, or a pharmaceutically acceptable salt thereof, includes those wherein A is

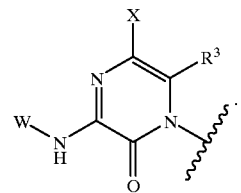

wherein $R^3$ is $CH_3$ or Cl.

A subclass of compounds of this class, or a pharmaceutically acceptable salt thereof, includes those wherein $Y^1$, $Y^2$, $Y^3$, $Y^4$, $Y^5$, and $Y^6$ are independently hydrogen, $C_{1-4}$ alkyl, or $NH_2$; W is $R^1$; $R^1$ is $R^2(CH_2)_2$—; and $R^2$ is a 5- to 7-membered mono- or a 9- to 10-membered bicyclic heterocyclic ring or non-heterocyclic ring which can be saturated or unsaturated, wherein the heterocyclic ring contains from one to four heteroatoms selected from the group consisting of N, O, and S, and wherein the heterocyclic ring is unsubstituted.

In a group of compounds of this subclass, or a pharmaceutically acceptable salt thereof, $Y^1$, $Y^2$, $Y^3$, $Y^4$, $Y^5$, and $Y^6$ are independently hydrogen, methyl or $NH_2$; and W is

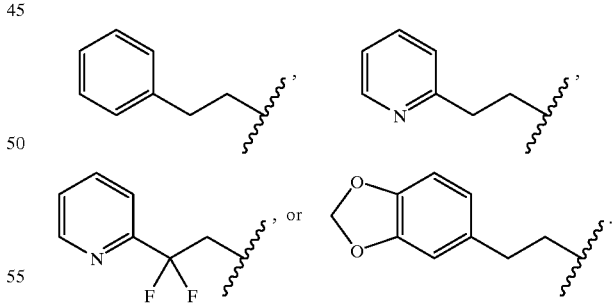

In a subgroup of this group of compounds, b is NH, $N(CH_3)$ or O, c is CH or N, d is CH, $C(NH_2)$, e is CH, f is N or CH, and g is CH or N.

Examples of this group are listed below in Table 1. Inhibitory activity of compounds of the invention is represented by "**", indicating Ki greater than or equal to 100 nM, or "*", indicating Ki less than 100 nM. Values are as determined according to the in vitro assay described later in the specification.

TABLE 1
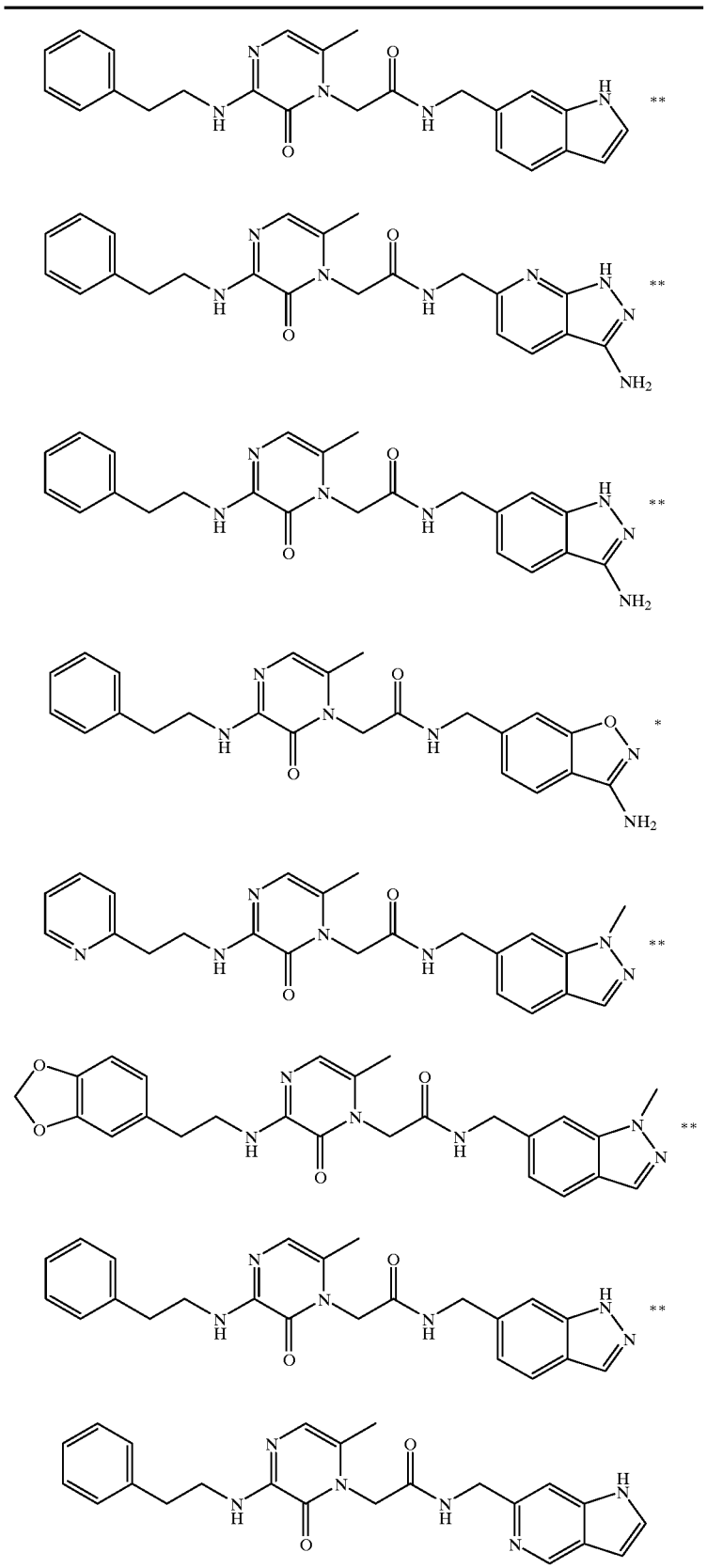

TABLE 1-continued

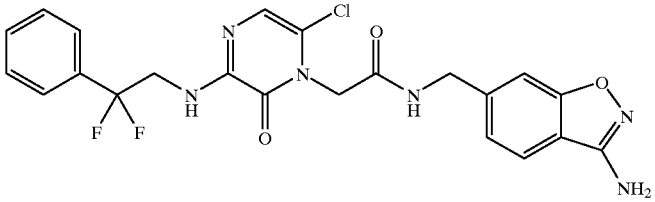

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-7}$cycloalkyl" is intended to include cyclopropyl, cyclobutyl, cyclopentyl, cyclohexyl and cycloheptyl, and the like.

The term "$C_{7-12}$ bicyclic alkyl" is intended to include bicyclo[2.2.1]heptyl (norbornyl), bicyclo[2.2.2]octyl, 1,1,3-trimethyl-bicyclo[2.2.1]heptyl (bornyl), and the like.

The term "aryl" as used herein except where noted, represents a stable 6- to 10-membered mono- or bicyclic ring system. The aryl ring can be unsubstituted or substituted with one or more of $C_{1-4}$ lower alkyl; hydroxy; alkoxy; halogen; amino. Examples of "aryl" groups include phenyl and naphthyl.

The term "heterocycle" or "heterocyclic ring", as used herein except where noted, represents a stable 5- to 7-membered mono- or bicyclic or stable 9- to 10-membered bicyclic heterocyclic ring system any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Bicyclic unsaturated ring systems include bicyclic ring systems which may be partially unsaturated or fully unsaturated. Partially unsaturated bicyclic ring systems include, for example, cyclopentenopyridinyl, benzodioxan, methylenedioxyphenyl groups. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiophenyl, oxazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl. Unsaturated heterocyclic rings may also be referred to hereinafter as "heteroaryl" rings.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Some abbreviations that may appear in this application are as follows.

| ABBREVIATIONS | |
| --- | --- |
| Designation | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| Activating Group | |
| HBT(HOBT or HOBt) | 1-hydroxybenzotriazole hydrate |
| Designation | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloric |
| EDC | 1-ethyl-3-(3-dimethylaminopropyl) carbodiimide hydrochloride |
| | Other |
| $(BOC)_2O$ $(BOC_2O)$ | di-t-butyl dicarbonate |
| $n\text{-}Bu_4N\text{+}F\text{-}$ | tetrabutyl ammonium fluoride |
| nBuLi (n-Buli) | n-butyllithium |
| DMF | dimethylformamide |
| $Et_3N$ (TEA) | triethylamine |
| EtOAc | ethyl acetate |
| TFA | trifluoroacetic acid |
| DMAP | dimethylaminopyridine |
| DME | dimethoxyethane |
| NMM | N-methylmorpholine |
| DPPA | diphenylphosphoryl azide |
| THF | tetrahydrofuran |
| DIPEA | diisopropylethylamine |
| | Amino Acid |
| Ile | Isoleucine |
| Phe | Phenylalanine |
| Pro | Proline |
| Ala | Alanine |
| Val | Valine |
| In vitro assay for determining proteinase inhibition | |

Assays of human α-thrombin and human trypsin were performed by the methods substantially as described in *Thrombosis Research*, Issue No. 70, page 173 (1993) by S. D. Lewis et al.

The assays were carried out at 25° C. in 0.05 M TRIS buffer pH 7.4, 0.15 M NaCl, 0.1% PEG. Trypsin assays also contained 1 mM $CaCl_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin ($K_m$=125 μM) and bovine trypsin ($K_m$=125 μM). p-Nitroanilide substrate concentration was determined from measurements of absorbance at 342 nm using an extinction coefficient of 8270 $cm^{-1}M^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≦0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in equation 1:

$$V_o/V_i = 1 + [I]/K_i \tag{1}$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The compounds of the invention are selective compounds, as evidenced by their inhibitory activity against human trypsin (represented by Ki).

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, of compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Coming Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinylpyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium bentzoate, sodium acetate, sodium chloride and the like. Disintegrators include, without limitation, starch methyl cellulose, agar, bentonite, xanthan gum and the like.

Typical uncoated tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

General Procedure for Making Compounds of the Invention

Compounds may be prepared, for example, by a common condensation reaction between a group having a carboxylic acid moiety and a group having an amino moiety, forming a peptide or amide bond. Compounds may be prepared by other means however, and suggested starting materials and procedures described below are exemplary only and should not be construed as limiting the scope of the invention.

In general, compounds having the general structure

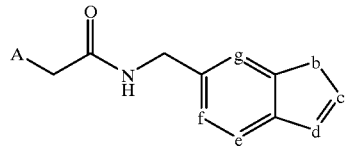

wherein the variables have the above-described meanings, can be prepared by reacting

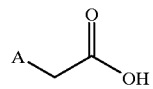

with

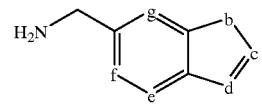

under conditions suitable for forming amide bond between the acid and the amine.

Suitable carboxylic acid starting materials for

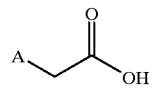

may be prepared according to the following procedures.

Carboxylic Acids

METHOD 1

Starting allylamine is condensed with acetaldehyde and cyanide in Step A to afford the aminonitrile. This is reacted in Step B with oxalyl chloride according to the method of Hoornaert [*J. Heterocyclic Chem.*, 20, 919, (1983)] to give the pyrazinone. The olefin is oxidatively cleaved with ruthenium tetraoxide and the resulting aldehyde is converted to the acid by an oxidizing agent such as chromic acid in Step C. The 3-chloro group is then displaced by an ammonia equivalent, in this case p-methoxybenzylamine in Step D. The remaining chlorine is removed by reduction with Raney nickel in Step E and in Step F the p-methoxybenzyl group is removed by treatment with a strong acid such as TFA.

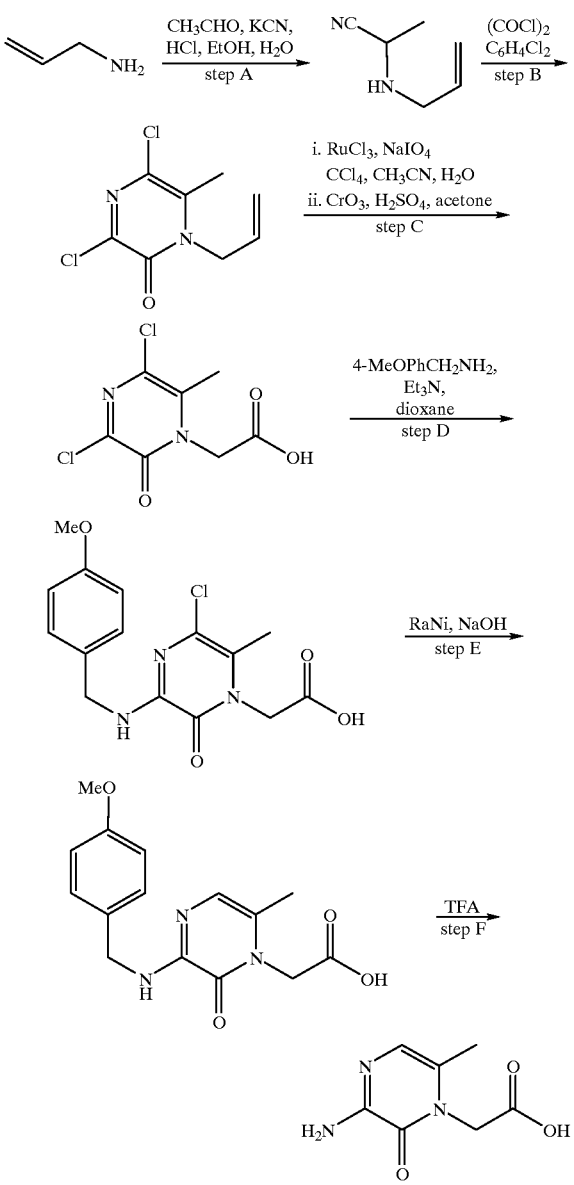

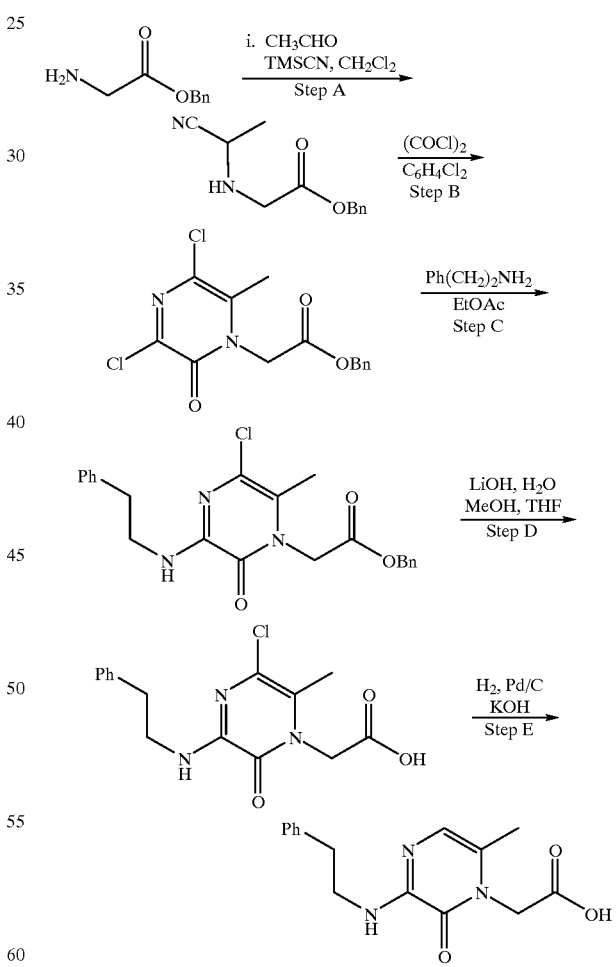

METHOD 2

The acid from METHOD 1, Step C is coupled to the appropriate amine. The 3-chloro group is then displaced by the appropriate amine and a protecting group is then removed, if necessary, to give the final product.

Modifications of the method will allow different W, $R^3$, and X groups contemplated by the scope of the broad claim below to be present by the use of an appropriate reagent or appropriately substituted starting material in the indicated synthetic step. Obvious variations and modifications of the method to produce similar and obvious variants thereof, will be apparent to one skilled in the art.

METHOD 3

An ester of glycine, in this case the benzyl ester, is condensed with acetaldehyde and cyanide in Step A to afford the aminonitrile. This is reacted in Step B with oxalyl chloride to give the pyrazinone. The 3-chloro group is then displaced by the appropriate amine, in this case phenethylamine, in Step C. The ester is hydrolyzed in Step D and the remaining chlorine is then removed by hydrogenolysis in Step E.

Typically, solution phase amide couplings may be used to form the final product, but solid-phase synthesis by classical Merrifield techniques may be employed instead. The addition and removal of one or more protecting groups is also typical practice.

Modifications of the method will allow different W, $R^3$, X and A groups contemplated by the scope of the broad claim below to be present by the use of an appropriate reagent or appropriately substituted starting material in the indicated synthetic step. For example the starting aldehyde in Step A can have as its side chain, ethyl, isopropyl, cyclopropyl, trifluoromethyl, and the like, to achieve the different operable values of $R^3$. Likewise, different W groups can be present by the use of an appropriate amine in Step D. Different X groups can be present by the omission of step E, and by the use of a reagent such as oxalyl bromide in step B. Obvious variations and modifications of the method to produce similar and obvious variants thereof, will be apparent to one skilled in the art.

METHOD 4

Starting allylamine is condensed with acetaldehyde and cyanide in Step A to afford the amninonitrile. This is reacted in Step B with oxalyl chloride according to the method of Hoornaert [*J. Hetero cyclic Chem.*, 20, 919, (1983)] to give the pyrazinone. The olefin is oxidatively cleaved with ruthenium tetraoxide and the resulting aldehyde is converted to the acid by an oxidizing agent such as chromic acid in Step C. The 3-chloro group is then displaced by the appropriate amine, in this case phenethylamine, in Step D and the remaining chlorine is then removed by reduction with Raney nickel in Step E.

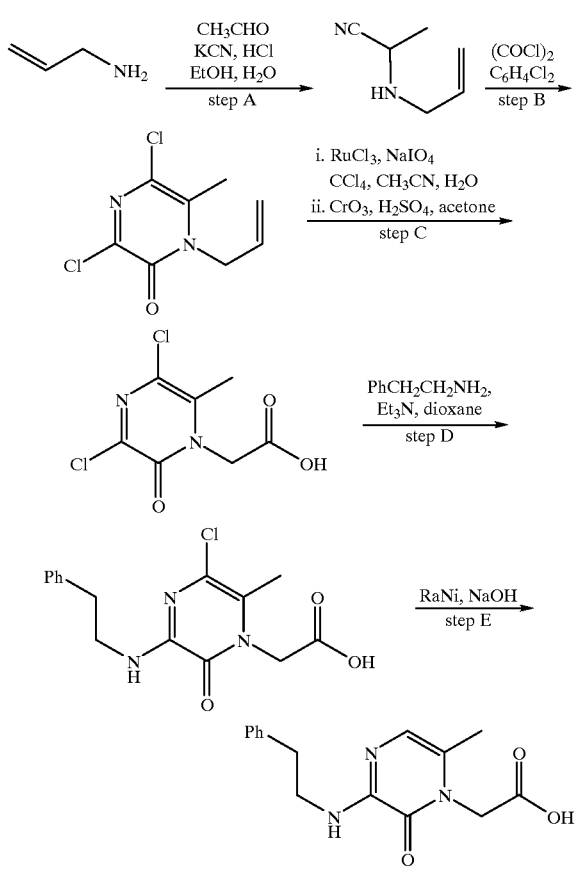

Amide couplings to form the compounds of this invention can be performed by the carbodiimide method. Other methods of forming the amide or peptide bond include, but are not limited to the synthetic routes via an acid chloride, azide, mixed anhydride or activated ester. Typically, solution phase amide couplings are performed, but solid-phase synthesis by classical Merrifield techniques may be employed instead. The addition and removal of one or more protecting groups is also typical practice.

Modifications of the method will allow different W, $R^3$, X and A groups contemplated by the scope of the broad claim below to be present by the use of an appropriate reagent or appropriately substituted starting material in the indicated synthetic step. For example the starting aldehyde in Step A can have as its side chain, ethyl, isopropyl, cyclopropyl, trifluoromethyl, and the like, to achieve the different operable values of $R^3$. Likewise, different W groups can be present by the use of an appropriate amine in Step D. Different X groups can be present by the omission of step E, and by the use of a reagent such as oxalyl bromide in step B. Obvious variations and modifications of the method to produce similar and obvious variants thereof, will be apparent to one skilled in the art.

METHOD 5

Formation of [RS]-3-benzyl-7-carboxymethyl-6-methyl-2-oxo-1,2,3,4-tetrahydro-1,7-naphthiridin-[7H]-8-one (5) is a useful intermediate for preparing compounds of the invention.

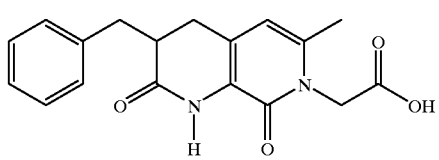

(5)

It is prepared as follows:

Step A: Ethyl 6-methyl-3-nitropyridone 4-carboxylate

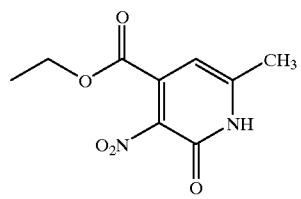

(5a)

To a slurry nitroacetamide ammonia salt (70.3 g, 581 mmol) in 400 mL of deionized water was added 100 g (633 mmol, 1.09 equiv.) of ethyl 2,4-dioxovalerate followed by a solution of piperdinium acetate (prepared by adding 36 mL of piperdine to 21 mL of acetic acid in 100 mL of water). The resulting solution was stirred at 40° C. for 16 h then cooled in an ice bath. The precipitated product was filtered and washed with 50 mL of cold water to afford the above pyridone as a yellow solid.

$^1$H NMR (CDCl$_3$) d 6.43 (s, 1H), 4.35 (q, J=7 Hz, 2H), 2.40 (s, 3H), 1.35 (t, J=7 Hz, 3H).

Step B: Ethyl 2-methoxy-6-methyl-3-nitropyridine 4-carboxylate

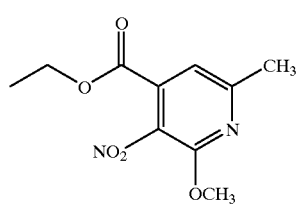

(5b)

A solution of the pyridone from step A (6.2 g, 27.4 mmol) in 50 mL of DCM was treated with 4.47 g (30.2 mmol) of solid trimethyloxonium tetrafluoroborate and the mixture was stirred at 40° C. until the reaction was judged to be complete by HPLC (typically 24–72 h). The reaction mixture was concentrated to one-third volume, loaded onto a silica gel column and eluted with 2:3 EtOAc/Hexane to afford the methoxy pyridine as a yellow liquid.

¹H NMR (CDCl₃) d 7.2 (s, 1H), 4.35 (q, J=7 Hz, 2H), 4.05 (s, 3H), 2.55 (s, 3H) 1.35 (t, J=7 Hz, 3H).

Step C: 4-Hydroxymethyl-2-methoxy-6-methyl-3-nitropyridine

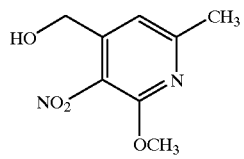

(5c)

To a −70° C. solution of ester from step B (5.4 g, 22.5 mmol) in 140 mL of DCM was added 56.2 mL (56.2 mmol) of DIBAL-H (1M in hexane) by dropping funnel. The resulting solution was stirred for 1 h then warmed to room temperature over an additional hour. The reaction mixture was quenched by the careful addition of saturated NaK tartrate. Stirring was continued for 30 min then the solid was filtered and washed with 100 mL of DCM. The filtrate was extracted with 2×50 mL of saturated NaK tartrate then brine (25 mL). The yellow solution was concentrated and chromatographed (2:3 EtOAc/Hexane) to afford the desired alcohol as a yellow solid.

¹H NMR (CDCl₃) d 7.00 (s, 1H), 4.70 (s, 2H), 4.05 (s, 3H), 2.50 (s, 3H), 2.10 (bs, 1H).

Step D: 4-Formyl-2-methoxy-6-methyl-3-nitropyridine

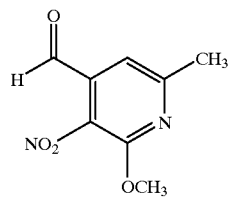

(5d)

To a −70° C. solution of oxalyl chloride (2.0 mL, 22 =mol) in 50 mL of DCM was added 3.4 mL (44 mmol) of DMSO in 10 mL of DCM by dropping funnel. After 2 min, the reaction mixture was treated with 3.99 g (20 mmol) of the alcohol from step C in 20 mL of DCM. The solution was stirred for an additional 15 min at −70° C., treated with 14 mL (50 mmol) of Et₃N and warned to ambient temperature over 90 min. The reaction was quenched with 100 mL of water and the two phases were separated. The aqueous phase was extracted with 100 mL of DCM and the combined organic extracts were washed with 50 mL of brine and dried over MgSO₄. The yellow solution was concentrated and chromatographed (2:3 EtOAc/Hexane) to afford the aldehyde as a yellow solid.

¹H NMR (CDCl₃) d 10.05 (s, 1H), 7.10 (s, 1H), 4.70 (s, 2H), 4.05 (s, 3H), 2.60 (s, 3H).

Step E: Methyl-2-benzyl-3-(4-[6-methyl-2-methoxy-3-nitropyridyl])-acrylate:

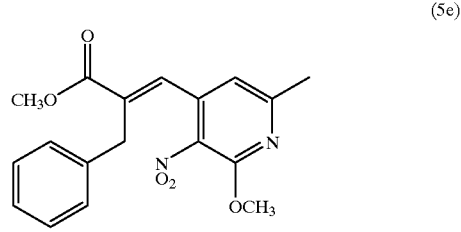

(5e)

To a 0° C. solution of 2-benzyl-trimethylphosphonoacetate (1.36 g, 5.0 mmol) in 25 mL of THF was added 145 mg (4.75 mmol) of NaH. The mixture was stirred for 30 min before the dropwise addition of 930 mg (4.75 mmol) of 4-formyl-2-methoxy-3-nitropyridine in 15 mL of THF. The solution was then heated at 50° C. for 3 h, cooled and evaporated. The residue was redissolved in 100 mL of EtOAc and quenched to pH=7 with saturated NH₄Cl. The organic phase was washed with brine and dried over MgSO₄. Column chromatography (2:3 EtOAc/Hexane) afforded the desired olefin as a mixture of E- and Z-isomers.

¹H NMR (CDCl₃) d 7.60 (s, 1H), 7.40–7.00 (m, 6H), 6.60 (2 singlets, 2H), 4.00 (2 singlets, 6H), 3.75 (2 singlets, 8H), 2.40 (2 singlets, 6H).

Step F: [RS]-3-benzyl-6-methyl-8-methoxy-2-oxo-1,2,3,4-tetrahydro-1,7-naphthiridine:

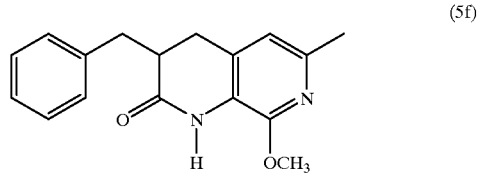

(5f)

To a solution of nitro olefin from step E (1.6 g, 4.75 mmol) in 50 mL of EtOAc was added 400 mg of 10% Pd©. Hydrogen gas was added and the solution was heated at 50° C. for 16. The reaction mixture was filtered through Celite and the filtrate evaporated. Column chromatography (2:3 EtOAc/Hexane) afforded the bicyclic lactam as a white solid.

¹H NMR (CDCl₃) d 7.45 (bs, 1H), 7.40–7.20 (m, 5H), 6.45 (s, 1H), 3.95 (s, 3H), 3.35 (dd, 1H), 2.80 (m, 2H), 2.60 (m, 2H), 2.40 (s, 3H).

Step G: [RS]-3-benzyl-6-methyl-2-oxo-1,2,3,4-tetrahydro-1,7-naphthiridin-[7H]-8-one:

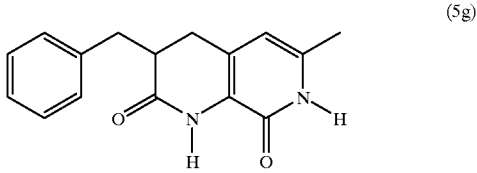

(5g)

To a 23° C. solution of methoxypyridine from step F (700 mg, 2.48 mmol) in 25 mL of dichloroethane was added 8.0 mL (8.0 mmol) of BBr₃ (1M in DCM). An insoluble gum precipitates within 5 min and the reaction was allowed to stir an additional 90 min before quenching to pH=8 with saturated NaHCO₃. The mixture was diluted with 100 mL of EtOAc and 10 mL THF. The aqueous phase was discarded and the organic solution was washed with 10 mL of water then 10 mL of brine. Evaporation of the solvent left a tan colored solid which was used without further purification.

$^1$H NMR (CDCl$_3$) d 8.20 (bs, 1H), 7.40–7.10 (m, 5H), 5.88 (s, 1H), 3.35 (dd, 1H), 2.80–2.50 (m, 4H), 2.25 (s, 3H).

Step H: [RS]-3-benzyl-7-t-butoxycarbonylmethyl-6-methyl-2-oxo-1,2,3,4-tetrahydro-1,7-naphthiridin-[7H]-8-one:

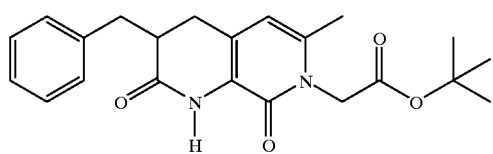

(5h)

To a 23° C. solution of pyridone from step G (630 mg, 2.5 mmol) in 20 mL of DMF was added 812 mg (2.5 mmol) of Cs$_2$CO$_3$ and 0.37 mL (2.5 mmol) of tert-butyl bromoacetate. The reaction mixture was allowed to stir for 16 h before removal of the solvent in vacuo. The mixture was diluted with 100 mL of EtOAc and 25 mL water. The aqueous phase was discarded and the organic solution was washed with 20 mL of brine. Evaporation of the solvent and chromatography (1:1 EtOAc/Hexane) of the resulting oil left the alkylated pyridone as a white solid.

$^1$H NMR (CDCl$_3$) d 7.84 (bs, 1H), 7.33–7.17 (m, 5H), 5.87 (s, 1H), 4.79 (q, J=17.2 Hz, 2H), 3.36 (dd, J=4.1,13.5 Hz, 1H), 2.79 (m, 1H), 2.65 (m, 2H), 2.48 (m, 1H), 2.23 (s, 3H), 1.48 (s, 9H).

Step I: [RS]-3-benzyl-7-carboxymethyl-6-methyl-2-oxo-1,2,3,4-tetrahydro-1,7-naphthiridin-[7H]-8-one:

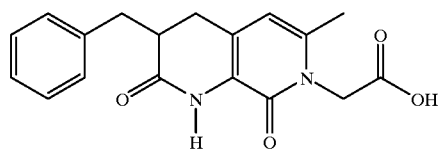

(5i)

To a 0° C. solution of ester from step H (310 mg, 0.85 mmol) in 30 mL of DCM was added 8 mL of trifluoroacetic acid. The reaction mixture was allowed to stir to ambient temperature over 5 h before removal of the solvent in vacuo. The resulting solid was azeotroped with benzene, EtOAc then ether. This process yielded the desired carboxylic acid as a white solid.

$^1$H NMR (DMSO-d6) d 8.92 (bs, 1H), 7.35–7.10 (m, 5H), 6.04 (s, 1H), 4.75 (q, J=17.2 Hz, 2H), 3.16 (dd, J=4.2,13.7 Hz, 1H), 2.79 (m, 1H), 2.65–2.40 (m, 3), 2.1 (s, 3H).

EXAMPLE 1

Amides of 5-aminomethyl-7-azaindole were prepared as follows:

Step A: 7-Aza-5-bromoindoline

See Van Der Plas et al., *Tetrahedron* 1989, 45, 803, and Taylor et al. ibid. 1987, 43, 5145. NBS (2.71 g, 15.2 mmol) was added to a stirred solution of 7-azaindoline (1.83 g, 15.2 mmol, in chloroform (200 mL). After 1 h, the reaction mixture was washed with 10% sodium metabisulfite solution, dried (Na$_2$SO$_4$), filtered through a pad of silica (eluting with ethyl acetate) and evaporated in vacuo to give the title compound:

$^1$H NMR (CDCl$_3$) δ 3.09 (t, J=8.5 Hz, 2H), 3.74 (t, J=8.5 Hz, 2H), 5.00 (br s, 1H), 7.32 (s, 1H), 8.13 (s, 1H).

Step B: 7-Aza-5-cyanoindoline

A stirred mixture of 7-aza-5-bromoindole (171 mg, 0.86 mmol), zinc cyanide (61 mg, 0.52 mmol) and tetrakis (triphenyl-phosphine)palladium(0) (60 mg, 0.052 mmol) in DMF (1 mL) was heated to 80° C. under argon. After 5 h, the reaction mixture was partitioned between methylene chloride and water. The organic layer was dried (MgSO$_4$) and evaporated in vacuo. The crude product was purified by flash column chromatography on silica (80% ethyl acetate/hexanes) to give the title compound:

$^1$H NMR (CDCl$_3$) δ 3.07 (m, 2H), 3.65 (t, J=8.4 Hz, 2H), 4.52 (br s, 1H), 7.31 (s, 1H), 7.85 (s, 1H).

Step C: 5-Aminomethyl-7-azaindoline dihydrochloride

A suspension of 7-aza-5-cyanoindoline (98 mg, 0.68 mmol) and 10% palladium on carbon (50 mg) in methanol (10 mL) and 6 M HCl (1 mL) was shaken on a Parr apparatus under hydrogen (55 psi) for 16 h. The mixture was filtered through celite and evaporated in vacuo to give the title compound:

$^1$H NMR (CD$_3$OD) δ 3.30 (obscured t, 2H), 3.95 (t, J=8.2 Hz, 2), 4.03 (s, 2H), 7.66 (s, 2H).

Step D: 3-(2-Phenethylamino)-6-methyl-1-(5-methylcarbox-amidomethyl-7-azaindolinyl)-pyrazinone bis-TFA salt The title compound was prepared using standard procedures from 3-(2-Phenethylamino)-6-methyl-1-carboxymethylpyrazinone and 5-aminomethyl-7-azaindoline dihydro chloride.

Step E: 3-(2-Phenethylamino)-6-methyl-1-(5-methylcarbox-amidomethyl-7-azaindolyl)-pyrazinone bis-TFA salt

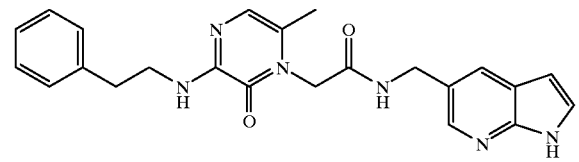

A mixture of manganese dioxide (9 mg, 0.1 mmol) and 3-(2-phenethylamino)-6-methyl-1-(5-methylcarboxamidomethyl-7-azaindolinyl)-pyrazinone bis-TFA salt (12.3 mg, 0.02 mmol) in DMF (1 mL) was stirred for 2 h. Methanol was added and the mixture was filtered through celite and evaporated in vacuo. The residue was dissolved in a mixture of methanol and 1 M HCl in ether and was evaporated in vacuo. The crude product was purified by preparative HPLC (C$_{18}$, acetonitrile/water, 0.1% TFA) to give the title compound:

$^1$H NMR (CD$_3$OD) δ 2.18 (s, 3H), 3.00 (t, J=7.4 Hz, 2H), 3.67 (t, J=7.4 Hz, 2H), 4.58 (s, 2H), 4.78 (s, 2H), 6.54 (s, 1H), 6.63 (d, J=3.7 Hz, 1H), 7.20–7.7.32 (m, 5H), 7.53 (d, J=3.7 Hz, 1H), 8.25 (s, 1H), 8.27 (s, 1H).

EXAMPLE 2

Amides of 3-amino-5-aminomethyl-7-azaindazole were prepared as follows:

Step A: 2-amino-3.5-dicyanopyridine

A mixture of 2-amino-6-chloro-3,5-dicyanopyridine (*Synth. Comm.* 1993, 2605, 15.0 g, 84 mmol) and 10% palladium on carbon (10.0 g) in dioxane (150 mL) was shaken on a Parr apparatus under hydrogen (55 psi) for 16 h. More catalyst (7.5 g) was added and after a further 4 h the reaction mixture was filtered through celite washing through with ethanol and evaporated in vacuo. The residue was partitioned between methylene chloride and 1 M HCl. The insoluble material was collected by filtration and dried to give the title compound. The methylene chloride layer was washed with brine, dried (Na$_2$SO$_4$) and evaporated in vacuo to give additional product:

$^1$H NMR (DMSO) δ 7.93 (br s, 2H), 8.41 (d, J=2.2 Hz, 1H), 8.56 (d, J=2.2 Hz, 1H).

Step B: 2-Chloro-3,5-dicyanopyridine

Acetic acid (37 mL) was added over 10 min to sodium nitrite (13.4 g, 0.194 mol) with stirring. Concentrated sulfuric acid (12.3 mL) was added over 5 min to the resulting thick slurry which was then cooled to 0° C. In a separate flask, pyridinium hydrochloride (14.4 g, 0.125 mol) was added to a stirred mixture of 2-amino-3,5-dicyanopyridine (4.0 g, 27.75 mmol) in acetic acid (55 mL) and the resulting mixture was cooled to 0° C. to give a thick slurry. The nitrite slurry was added to the aminopyridine slurry over 5 min with stirring at 0° C. Acetic acid (50 mL) was added and the thick slurry was warmed to rt. After 1 h at rt the mixture was warmed to 50° C. and after a further 1 h, it was poured into an ice/water mixture (500 mL). The aqueous mixture was extracted with methylene chloride (4 times) and the combined extracts were dried (Na$_2$SO$_4$) and evaporated to a yellow solid. The crude product was purified by chromatography on silica (chloroform/methanol gradient, 1–3% methanol) to give the title compound as a solid:

$^1$H NMR (CDCl$_3$) δ 8.34 (d, J=2.2 Hz, 1H), 8.88 (d, J=2.2 Hz, 1H).

Step C: 5-Cyano-3-amino-7-azaindazole

Hydrazine hydrate (55%, 125 μL, 2.20 mmol) was added to a stirred suspension of 2-chloro-3,5-dicyanopyridine (240 mg, 1.47 mmol) and triethylamine (205 μL, 1.47 mmol) in ethanol (3 mL) and the resulting red mixture was heated to 60° C. After 16 h the mixture was cooled and filtered to give the title compound:

$^1$H NMR (DMSO) δ 5.94 (s, 2H), 8.61 (d, J=1.8 Hz, 1H), 8.66 (d, J=1.8 Hz, 1H), 12.63 (s, 1H).

Step D: 5-Aminomethyl-3-amino-7-azaindazole hydrochloride

The title compound was prepared from 5-cyano-3-amino-7-azaindazole using the procedures of Example 2, Step C, as a red solid:

LRMS=163.2 (M)$^+$.

Step E: 3-(2-Phenethylamino)-6-methyl-1-(5-methylcarboxamidomethyl-3-amino-7-azaindazolyl)-pyrazinone

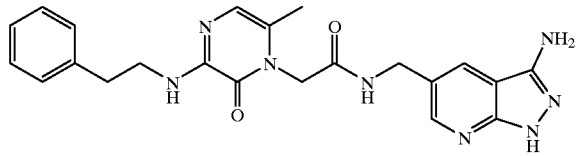

The title compound was prepared using standard procedures from 3-(2-phenethylamino)-6-methyl-1-carboxymethylpyrazinone and 5-aminomethyl-3-amino-7-azaindazole hydrochloride:

LRMS=433.2 (M+1).

EXAMPLE 3

Preparation of 3-(2-Phenethylamino)-6-methyl-1-(3-amino-6-methylcarboxamidomethylindazolyl)-pyrazinone

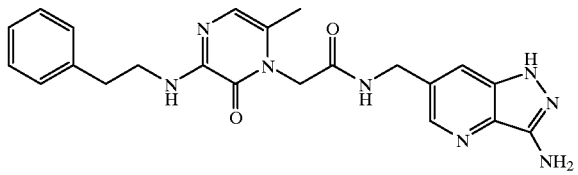

The title compound was prepared from 4-bromo-2-fluorobenzonitrile using the procedures of Example 1, Step B followed by Example 2, Steps C–E:

HRMS (FAB) C23H26N7O2 (M+1) calcd. 432.2142. Found: 432.2146.

EXAMPLE 4

Preparation of 3-(2-Phenethylamino)-6-methyl-1-(3-amino-6-methylcarboxamidomethyl-7-aza-indazolyl)-pyrazinone bis-TFA salt

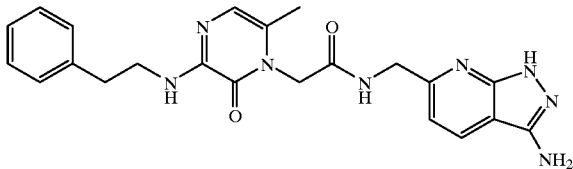

Step A: 2-Chloro-6-chloromethyl-3-cyanopyridine

NCS (1.44 g, 10.8 mmol) and benzoyl peroxide (238 mg, 0.98 mmol) were added to a stirred solution of 2-chloro-3-cyano-6-methyl-pyridine (750 mg, 4.92 mmol) in benzene (35 mL) and the mixture was heated to reflux. After 4 h, the mixture was cooled and filtered. The filtrate was diluted with ethyl acetate and was washed with sodium metabisulfite solution, water and brine, dried (Na$_2$SO$_4$) and evaporated in vacuo. The residue was purified by chromatography on silica (chloroform) to give the title compound:

$^1$H NMR (CDCl$_3$) δ 4.68 (s, 2H), 7.62 (d, J=7.9 Hz, 1H), 8.06 (d, J=7.9 Hz, 1H).

Step B: 6-Azidomethyl-2-chloro-3-cyanopyridine

A mixture of 2-chloro-6-chloromethyl-3-cyanopyridine (600 mg, 3.21 mmol) and sodium azide (229 mg, 3.53 mmol) in DMF (12 mL) were stirred at 50° C. for 30 min. The mixture was cooled and partitioned between ethyl acetate and water. The organic layer was washed with water (2 times) and brine, dried (Na$_2$SO$_4$) and evaporated in vacuo. The residue was purified by chromatography on silica (chloroform) to give the title compound as an oil:

$^1$H NMR (CDCl$_3$) δ 4.58 (s, 2H), 7.47 (d, J=7.9 Hz, 1H), 8.03 (d, J=7.9 Hz, 1H),

Step C: 3-Amino-6-azidomethyl-7-azaindazole

The title compound was prepared from 6-azidomethyl-2-chloro-3-cyanopyridine using the procedures of Example 2, Step C, as a tan solid:

$^1$H NMR (DMSO) δ 4.52 (s, 2H), 5.56 (s, 2H), 6.98 (d, J=8.1 Hz, 1H), 8.12 (d, J=8.1 Hz, 1H), 11.97 (s, 1H).

Step D: 3-Amino-6-aminomethyl-7-azaindazole

A mixture of 3-amino-6-azidomethyl-7-azaindazole (60 mg, 0.317 mmol), triphenylphosphine (416 mg, 1.59 mmol) and water (86 mg, 4.76 mmol) in THF (10 mL) was stirred for 64 h. The solvent was evaporated in vacuo and the residue was purified by chromatography on silica (chloroform/ammonia, methanol gradient, 5–10% methanol) to give the title compound as a yellow solid:

$^1$H NMR (CDCl$_3$+CD$_3$OD) δ 4.03 (s, 2H), 6.98 (d, J=8.1 Hz, 1H), 7.92 (d, J=8.1 Hz, 1H).

Step E: 3-(2-Phenethylamino)-6-methyl-1-(3-amino-6-methylcarbox-amidomethyl-7-aza-indazolyl)-pyrazinone bis-TFA salt The title compound was prepared using standard procedures from 3-(2-phenethylamino)-6-methyl-1-carboxyrnethylpyrazinone and 3-amino-6-aminomethyl-7-azaindazole.

HRMS (FAB) C$_{22}$H$_{25}$N$_8$O$_2$ (M+1) calcd. 433.2095. Found: 433.2112.

EXAMPLE 5

Preparation of 3-(2-Phenethylamino)-6-methyl-1-(3-amino-6-methylcarboxamidomethyl-1,2-benzisoxazolyl)-pyrazinone:

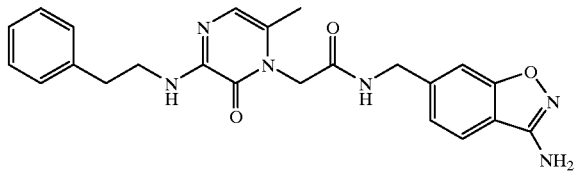

Step A: O-(2,5-Dicyanophenyl)-acetophenone oxime

Acetophenone oxime (0.58 g, 4.29 mmol) was added to a stirred 1M potassium t-butoxide in THF (4.49 mL). After 30 min a solution of 2,5-dicyanofluorobenzene (0.57 g, 3.90 mmol) in THF (10 mL) was added over 5 min. After 16 h the reaction was quenched with saturated ammonium chloride solution (5 mL) and the volatiles were evaporated in vacuo. The residue was partitioned between ethyl acetate and brine and the organic layer was dried (Na$_2$SO$_4$) and evaporated in vacuo to give the title compound as a solid:

$^1$H NMR (CDCl$_3$) δ 2.57 (s, 3H), 7.36 (dd, J=1.1 and 8.0 Hz, 1H), 7.49 (m, 3H), 7.69 (d, J=8.0 Hz, 1H), 7.77 (dd, J=2.2 and 8.0 Hz, 2H), 8.00 (d, J=1.1 Hz Step B: 3-Amino-6-cyano-1 2-benzisoxazole A stirred mixture of O-(2,5-dicyanophenyl)-acetophenone oxime (0.92 g, 3.5 mmol) in ethanol (10 mL) and 3 M HCl (10 mL) was heated to reflux for 3 h. The mixture was cooled and concentrated in vacuo. The residual aqueous mixture was partitioned between ethyl acetate and saturated sodium bicarbonate solution. The organic layer was washed with brine, dried (Na$_2$SO$_4$) and evaporated in vacuo to give the title compound as a yellow solid:

Step C: 3-Amino-6-aminomethyl-1,2-benzisoxazole

Borane methylsulfide complex (2 M in THF, 1.98 mL) was added to a stirred refluxing solution of 3-amino-6-cyano-1,2-benzisoxazole (210 mg, 1.32 mmol) in DME (10 mL). After 45 min excess methyl sulfide was evaporated and the reaction mixture was cooled and quenched with 1M HCl solution (10 mL). The mixture was stirred for 30 min and then was neutralised with sodium bicarbonate solution and concentrated to dryness. The residue was triturated with 5% methanol/chloroform, filtered and the filtrate evaporated in vacuo. The residue was purified by chromatography on silica (5% methanol, chloroform/ammonia) to give the title compound as a yellow solid:

$^1$H NMR (CDCl$_3$+CD$_3$OD) δ 4.80 (s, 2H), 7.20 (dd, J=1.1 and 8.1 Hz, 1H), 7.37 (s, 1H), 7.53 (d, J=8.1 Hz, 1H).

Step D: 3-(2-Phenethylamino)-6-methyl-1-(3-amino-6-methyl-carboxamidomethyl-1,2-benzisoxazolyl)-pyrazinone The title compound was prepared using standard procedures from 3-(2-phenethylamino)-6-methyl-1-carboxymethylpyrazinone and 3-amino-6-aminomethylbenzisoxazole.

LRMS (FAB) C$_{23}$H$_{25}$N$_6$O$_3$ 433.3 (M+1).

EXAMPLE 6

Preparation of 3-(2-Phenethylamino)-6-methyl-1-(3-amino-6-methylcarboxamidomethylindazolyl)-pyrazinone bis-TFA salt

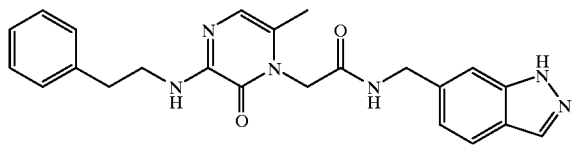

Step A: 6-Cyanoindazole

A solution of sodium nitrite (218 mg, 3.16 mmol) in water (1 mL) was added dropwise over 2 min to a stirred suspension of 3-amino-6-cyanoindazole (250 mg, 1.58 mmol) in water (1 mL) and acetic acid (2 mL) at 0° C. The resulting thick suspension was warmed to rt. After 16 h the mixture was cooled to 0° C. and the solids were collected by filtration, washing with cold water. The solids were suspended in 0.1 M HCl (4 mL), DME (3 mL) was added and the resulting mixture was stirred and heated to 80° C. for 1.5 h. The reaction was cooled and concentrated to ⅓ the volume. The residue was neutralised with sodium bicarbonate and extracted with ethyl acetate. The ethyl acetate layer was washed with water and brine, dried (Na$_2$SO$_4$) and evaporated in vacuo. The residue was purified by chromatography on silica (5:1 chloroform/ethyl acetate) to give the title compound as a yellow solid:

LRMS=143.1 (M)$^+$; $^1$H NMR (CDCl$_3$) δ 7.39 (dd, J=1.1 and 8.3 Hz, 1H), 7.87 (dd, J=0.9 and 8.3 Hz, 1H), 7.94 (dd, J=0.9 and 2.1 Hz, 1H), 8.21 (d, J=0.9 Hz, 1H).

Step B: 6-Aminomethylindazole dihydrochloride

The title compound was prepared using the procedures of Example 2, Step C, as a solid:

$^1$H NMR (CD$_3$OD) δ 4.26 (s, 2H), 7.23 (d, J=8.4 Hz, 1H), 7.67 (s, 1H), 7.87 (d, J=8.4 Hz, 1H), 8.11 (d, J=0.9 Hz, 1H).

Step D: 3-(2-Phenethylamino)-6-methyl-1-(3-amino-6-methyl-carboxamidomethylindazolyl)-pyrazinone bis-TFA salt The title compound was prepared using standard procedures from 3-(2-phenethylamino)-6-methyl-1-carboxymethylpyrazinone and 3-amino-6-aminomethylindazole dihydrochloride.

HRMS (FAB) C23H25N6O2 (M+1) calcd. 417.2033. Found: 417.2038.

EXAMPLE 7

Amides of 5-aminomethylindazole were prepared as follows:

Step A: 5-Cyano-2-fluorobenzaldehyde

To a solution of 5-bromo-2-fluorobenzaldehyde (1.93 g, 9.51 mmol) in DMF (4 mL) was added copper(I) cyanide (0.98 g, 10.93 mmol). The mixture was heated to 190 ° C. and stirred for 5 h. The dark brown reaction mixture was poured into a solution containing ferric chloride (3.0 g), conc. HCl (0.93 mL) and water (6 mL) and warmed to 65 ° C. for 20 min. The mixture was partitioned between toluene (20 mL) and water (20 mL). The organic was washed with diluted HCl (25 mL), water (20 mL), 10% sodium hydroxide (25 mL), dried over magnesium sulfate, and concentrated to provide a solid product:

$^1$H NMR (CDCl$_3$) δ 10.34 (m, 1H), 8.21 (m, 1H), 7.90 (m, 1H), 7.35 (m, 1H).

Step B: 5-Cyanoindazole

5-Cyano-2-fluorobenzaldehyde (512 mg, 3.43 mmol) was dissolved in hydrazine hydrate (25 mL) at room temperature and the solution left to stand overnight. To this reaction mixture was added methylene chloride (30 mL). The mixture was purified by filtration through a pad of silica eluting with methylene chloride, concentrated in vacuo to afford a white solid:

$^1$H NMR (DMSO) δ 8.40 (s, 1H), 8.25 (s, 1H), 7.69 (m, 2H).

Step C: 5-Aminomethylindazole

To a solution-of LiAlH$_4$ (0.76 g, 20.1 mmol) in THF (10 mL) cooled to 0° C. was added a solution of 5-cyanoindazole (0.64 g, 4.47 mmol) in THF (10 mL) dropwise. After 0.5 h the reaction mixture was warmed to reflux for 2 h, then cooled to 0° C. and quenched by the careful addition of water (0.76 mL), 1.0 N sodium hydroxide (0.76 mL), and water (2.28 mL). This mixture was filtered through a pad of celite and washed with THF/MeOH (3:1, 300 mL). Removal of the solvent in vacuo provided a solid which was purified via flash column chromatography (25× 150 mm column; elution with MeOH:CH$_2$Cl$_2$:CH$_2$Cl$_2$ saturated with NH$_3$, 10:60:30). This afforded the title compound as a light yellow solid:

$^1$H NMR (CDCl$_3$) δ 10.0 (s, 1H), 8.61 (s, 1H), 8.15 (s, 1H), 7.90–7.60 (m, 2H), 4.92 (s, 2H).

Step D: 3-(2-Phenylethylamino)-6-methyl-1-(5-methylenecarboxamidomethylindazolyl)-pyrazinone

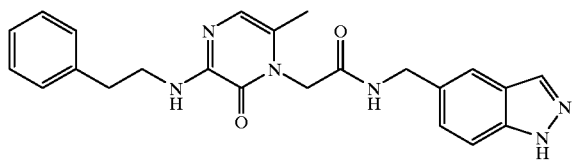

The title compound was prepared from 5-aminomethylindazole using standard procedures:

HRMS (FAB-POS M+1): calcd 417.2033 found 417.2043; Analysis: calculated for C$_{23}$H$_{24}$N$_6$O$_2$ 0.1 TFA; C65.12 H5.68 N19.64; Found: C65.49 H5.62 N19.28.

EXAMPLE 8

Amides of 5-aminomethyl-1-methylindazole were prepared as follows:

Step A: 5-Cyano-1-methylindazole

To a solution of 5-cyano-2-fluorobenzaldehyde (0.50 g, 3.35 mmol) in ether (5 mL) was added methyl hydrazine (0.178 µL, 3.35 mmol) dropwise at room temperature. The mixture was stirred at room temperature for 1 h and concentrated in vacuo to give the hydrazone as a yellow solid. This solid was fused at 230° C. for 10 min, cooled to rt, dissolved in CH$_2$Cl$_2$ and purified by filtration through a pad of silica (eluant CH$_2$Cl$_2$:MeOH; 19:1) to afford the title compound as a light yellow solid: $^1$H NMR (DMSO) δ 8.38 (s, 1H), 8.23 (s, 1H), 7.84 (d, J=8.8 Hz, 1H), 7.71 (d, J=8.8 Hz, 1H), 4.09 (s, 3H).

Step B: 5-Aminomethyl-1-methylindazole

The title compound was prepared according to the method described in Example 7, Step C, 5-cyano-1-methylindazole as a starting material:

$^1$H NMR (CDCl$_3$) d 7.93 (s, 1H), 7.63 (s, 1H), 7.36 (s, 2H), 4.72 (s, 3H), 4.07 (s, 2H); Cl-MS: m/e=162.10 (M+1).

Step C: 3-(2-Phenylethylamino)-6-methyl-1-(1-methyl-5-methylenecarboxamidomethylindazolyl)-pyrazinone

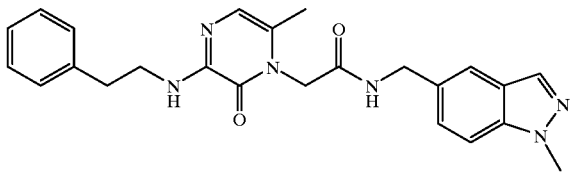

The title compound was prepared from 5-aminomethyl-1-methylindazole using standard procedures:

HRMS (FAB-POS M+1): calcd 431.2190 found 431.2179; Analysis: calculated for C$_{24}$H$_{26}$N$_6$O$_2$ 0.30 H$_2$O; C66.12 H6.15 N19.28; Found: C66.07 H5.91 N18.95.

EXAMPLE 9

Amides of 6-aminomethyl-1-methylindazole were prepared as follows:

Step A: 4-cyano-2-fluorobenzaldehyde

The title compound was prepared according to the method described in Example 7, Step A, 4-bromo-2-fluorobenzaldehyde as a starting material:

$^1$H NMR (DMSO) δ 10.23 (s, 1H), 8.10–7.86 (m, 3H).

Step B: 6-Cyano-1-methylindazole

The title compound was prepared according to the method described in Example 8, Step A, 4-cyano-2-fluorobenzaldehyde and methyl hydrazine as starting materials: $^1$H NMR (CDCl$_3$) δ 8.07 (s, 1H), 7.83 (d, J=8.2 Hz, 1H), 7.79 (s, 1H), 7.37 (d, J=8.3 Hz, 1H), 4.14 (s, 3H).

Step C: N-methyl-6-aminomethylindazole

The title compound was prepared according to the method described in Example 7, Step C, 6-cyano-1-methylindazole as a starting material: $^1$H NMR (CDCl$_3$) δ 7.94 (s, 1H), 7.68 (d, J=7.3 Hz, 1H), 7.37 (s, 1H), 7.09 (d, J=7.2 Hz, 1H), 4.07 (s, 3H), 4.04 (s, 2H).

Step D: 3-[2-(2-pyridyl)ethylamino]-6-methyl-1-(1-methyl-6-methylenecarboxamidomethylindazolyl)-pyrazinone

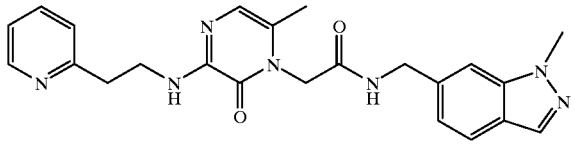

The title compound was prepared from 6-aminomethyl-1-methylindazole using standard procedures:

HRMS (FAB-POS M+1): calcd 432.2164 found 432.2142; Analysis: calculated for C$_{23}$H$_{25}$N$_7$O$_2$ 0.50 HOAc; C62.45 H5.90 N21.25; Found: C62.74 H5.65 N20.93

EXAMPLE 10

Preparation of 3-[2-(3,4-methylenedioxyphenyl)ethylamino]-6-methyl-1-(1-methyl-6-methylenecarboxamidomethylindazolyl)-pyrazinone

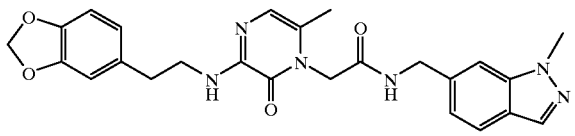

The title compound was prepared from 6-aminomethyl-1-methylindazole using standard procedures:

HRMS (FAB-POS M+1): calcd 475:2088 found 475.2102; Analysis: calculated for C$_{25}$H$_{26}$N$_6$O$_4$ 0.15 CHCl$_3$; C62.62 H5.99 N16.08; Found: C62.84 H5.61 N15.88

EXAMPLE 11

Preparation of 3-(2-Phenethylamino)-6-methyl-1-(6-methylcarboxamidomethylindolyl)-pyrazinone

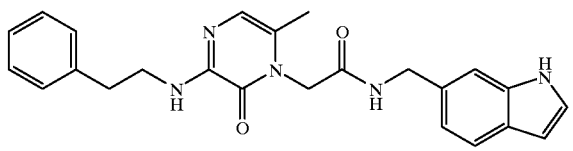

The title compound was prepared from 6-aminomethylindole using standard procedures:

HRMS (FAB) $C_{24}H_{26}N_5O_2$ (M+1) calcd. 416.2081. Found: 416.2094.

EXAMPLE 12

Tablet Preparation

Tablets containing 25.0, 50.0, and 100.0 mg., respectively, of the following active compounds are prepared as illustrated below (compositions A–I). Active I is 3-(2-Phenethylamino)-6-methyl-1-(3-amino-6-methylcarboxamidomethylindazolyl)-pyrazinone; Active II is 3-(2-Phenethylamino)-6-methyl-1-(3-amino-6-methylcarboxamidomethyl-7-aza-indazolyl)-pyrazinone bis-TFA salt; Active III is 3-(2-Phenethylamino)-6-methyl-1-(3-amino-6-methylcarboxamidomethyl-1,2-benzisoxazolyl)-pyrazinone; and Active IV is 3-(2-Phenethylamino)-6-methyl-1-(3-amino-6-methylcarboxamidomethylindazolyl)-pyrazinone bis-TFA salt.

| Component | 0.25 mg | 2 mg | 10 mg | 50 mg |
|---|---|---|---|---|
| Active IV | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet Preparation via Direct Compression

Active IV, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation via Dry Granulation

Alternatively, a dry powder blend is compacted under modest forces and remilled to afford granules of specified

| Component | A | B | C | D | E | F | G | H | I |
|---|---|---|---|---|---|---|---|---|---|
| Active I | 25 | 50 | 100 | — | — | — | — | — | — |
| Active II | — | — | — | 25 | 50 | 100 | — | — | — |
| Active III | — | — | — | — | — | — | 25 | 50 | 100 |
| Microcrystalline cellulose | 37.25 | 100 | 200 | 37.25 | 100 | 200 | 37.25 | 100 | 200 |
| Modified food corn starch | 37.25 | 4.25 | 8.5 | 37.25 | 4.25 | 8.5 | 37.25 | 4.25 | 8.5 |
| Magnesium stearate | 0.5 | 0.75 | 1.5 | 0.5 | 0.75 | 1.5 | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 13

Tablet Preparation

Exemplary compositions of 3-(2-Phenethylamino)-6-methyl-1-(3-amino-6-methylcarboxamidomethylindazolyl)-pyrazinone bis-TFA salt tablets are shown below:

particle size. The granules are then mixed with magnesium stearate and tabletted as stated above.

EXAMPLE 14

Intravenous Formulations

Intravenous formulations of were prepared according to general intravenous formulation procedures.

| Component | Estimated range |
|---|---|
| Active IV | 0.12 –0.61 mg |
| D-glucuronic acid* | 0.5 –5 mg |
| Mannitol NF | 50 –53 mg |
| Water for injection | q.s. 1.0 mL |

1N sodium hydroxide is used to achieve a solution pH in the range of between 3.9–4.1.

Exemplary compositions A–C are as follows:

| Component | A | B | C |
| --- | --- | --- | --- |
| Active IV | 0.61mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1 N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base;
**0.25 mg free base;
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound of the formula

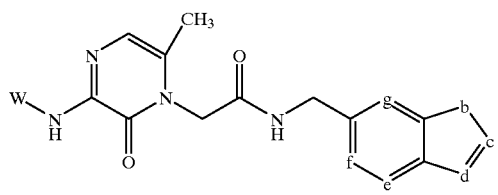

or a pharmaceutically acceptable salt thereof, wherein
b is $NY^1$ or O; c is $CY^2$ or N; d is $CY^3$; e is $CY^4$ or N; f is $CY^5$ or N; g is $CY^6$ or N; provided that 1) when e and f are N, g is $CY^6$, 2) when e and g are n, f is $CY^5$, and 3) when f and g are N, e is $CY^4$;
$Y^1$, $Y^2$, $Y^3$, $Y^4$, $Y^5$, and $Y^6$ are independently selected from the group consisting of hydrogen, methyl and $NH_2$; and
W is

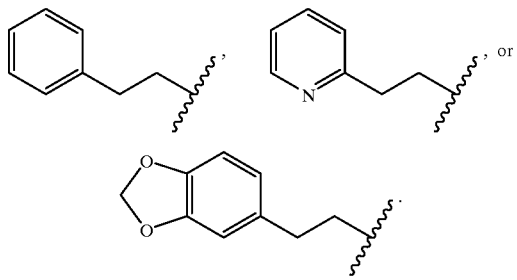

2. A compound of claim 1, or a pharmaceutically acceptable salt thereof, wherein b is NH, $N(CH_3)$ or O, c is CH or N, d is CH, $C(NH_2)$, e is CH, f is CH, and g is CH or N.

3. A compound of claim 2, or a pharmaceutically acceptable salt thereof, selected from the group consisting of

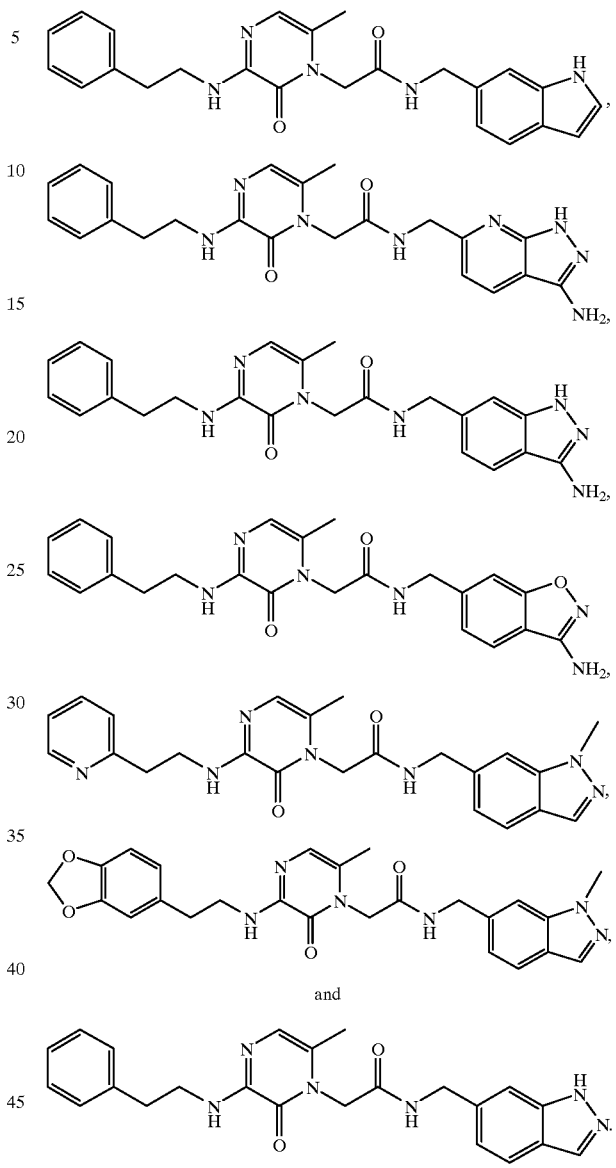

4. A pharmaceutical composition comprising a therapeutically effective amount of a compound of claim 1.

5. A method for inhibiting thrombus formation in blood comprising adding to the blood a composition of claim 4.

* * * * *